United States Patent [19]

Gay

[11] 4,228,289
[45] Oct. 14, 1980

[54] THIOLCARBAMATE DERIVATIVES OF 3-TRIHALOMETHYL-1,2,4-THIADIAZOLES

[75] Inventor: Walter A. Gay, Cheshire, Conn.

[73] Assignee: Olin Corporation, New Haven, Conn.

[21] Appl. No.: 102,052

[22] Filed: Dec. 10, 1979

Related U.S. Application Data

[62] Division of Ser. No. 6,060, Jan. 24, 1979.

[51] Int. Cl.³ .................... A01N 47/18; C07D 285/08
[52] U.S. Cl. .................................................. 548/128
[58] Field of Search ......................................... 548/128

[56] References Cited

U.S. PATENT DOCUMENTS

| | | | |
|---|---|---|---|
| 3,260,725 | 7/1966 | Schroeder | 548/128 |
| 3,324,141 | 6/1967 | Bernstein | 548/128 |
| 3,573,317 | 3/1971 | Smith | 548/128 |
| 3,629,275 | 12/1971 | Metzger et al. | 548/128 |
| 3,673,203 | 6/1972 | Miller | 548/128 |
| 3,720,684 | 3/1973 | Krenzer et al. | 548/128 |
| 3,764,685 | 10/1973 | Krenzer et al. | 548/128 |
| 3,822,280 | 7/1974 | Moser et al. | 548/128 |
| 3,873,299 | 3/1975 | Metzger et al. | 548/128 |
| 3,884,929 | 5/1975 | Smith | 548/129 |
| 3,904,619 | 9/1975 | D'Amico | 548/129 |
| 3,917,478 | 11/1975 | Moser et al. | 548/128 |
| 4,107,377 | 8/1978 | Tobin | 548/128 |

OTHER PUBLICATIONS

Yashida et al., Chem. Abstracts, vol. 79, Abstract No. 74937p (1973).

*Primary Examiner*—Alton D. Rollins
*Attorney, Agent, or Firm*—William A. Simons; Thomas P. O'Day

[57] ABSTRACT

Disclosed are selected thiolcarbamate derivatives of 3-trihalomethyl-1,2,4-thiadiazole compounds of the formula:

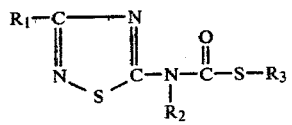

wherein $R_1$ is a $CCl_3$ or $CF_3$ group; $R_2$ is hydrogen or a lower alkyl group of 1 to 4 carbon atoms and $R_3$ is a lower alkyl group having 1 to 4 carbon atoms. These compounds are shown to have post-emergence herbicidal properties.

5 Claims, No Drawings

THIOLCARBAMATE DERIVATIVES OF 3-TRIHALOMETHYL-1,2,4-THIADIAZOLES

This is a division, of application Ser. No. 006,060, filed Jan. 24, 1979.

BACKGROUND OF THE INVENTION

1. Field of the Invention

This invention relates to selected thiolcarbamate derivatives of 3-trihalomethyl-1,2,4-thiadiazole compounds and their use as herbicides.

2. Description of the Prior Art

Various 3,5-substituted-1,2,4-thiadiazole compounds have been known to possess different types of pesticidal activity such as fungicidal, herbicidal, insecticidal, nematocidal and the like. For example, U.S. Pat. No. 3,884,929, which issued to Eric Smith on May 20, 1975, discloses the use of 3-trichloromethyl-5-N,N-di(lower-alkyl) dithiocarbamoyl as bactericides, fungicides and algaecides.

Furthermore, various 1,3,4-thiadiazole compounds have also been known to possess different types of pesticidal activity. For example, Chemical Abstracts 79:74937 discloses S-ethyl 5-trifluoromethyl-2-(1,3,4-thiadiazolyl) thiocarbamate or S-propyl 5-trifluoromethyl-2-(1,3,4-thiadiazolyl) thiocarbamate and their use as herbicides. However, it should be noted that 1,2,4-thiadiazoles and 1,3,4-thiadiazoles are treated as completely different classes of compounds by ordinarily skilled artisans in the pesticidal field because of their different modes of preparation, including the use of different starting materials.

BRIEF SUMMARY OF THE INVENTION

Accordingly, the present invention is directed to, as compositions of matter, selected thiolcarbamate derivatives of 3-trihalomethyl-1,2,4-thiadiazole compounds of the formula:

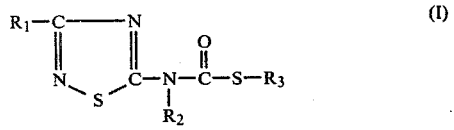
(I)

wherein $R_1$ is a $CCl_3$ or $CF_3$ group; $R_2$ is hydrogen or a lower alkyl group of 1 to 4 carbon atoms; and $R_3$ is a lower alkyl group having from 1 to 4 carbon atoms. The present invention is also directed to the use of these compounds as post-emergence herbicides.

DETAILED DESCRIPTION

The 5-thiolcarbamate derivative compounds of the present invention may be prepared by reacting the corresponding 5-amino substituent-3-trihalomethyl-1,2,4-thiadiazole with the desired lower alkyl chlorothiolformate, preferably in the presence of an acid acceptor such as potassium carbonate. This general reaction is illustrated below in equation (A) which shows the reaction of 5-amino-3-trichloromethyl-1,2,4-thiadiazole with ethyl chlorothiolformate:

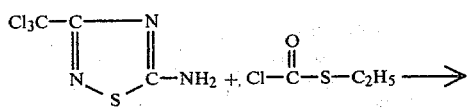
(A)

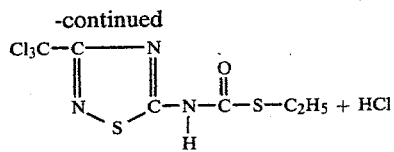

Suitable 5-amino substituent-3-trihalomethyl-1,2,4-thiadiazole reactants include, besides 5-amino-3-trichloromethyl-1,2,4-thiadiazole, 5-methylamino-3-trichloromethyl-1,2,4-thiadiazole and 5-amino-3-trifluoromethyl-1,2,4-thiadiazole. 5-Amino-3-trichloromethyl and 5-methylamino-3-trichloromethyl-1,2,4-thiadiazole are both described in U.S. Pat. No. 3,260,725, issued to H. A. Schroeder on July 12, 1966, and are made by reacting 5-chloro-3-trichloromethyl-1,2,4-thiadiazole with ammonia or methylamine, respectively. 5-Amino-3-trifluoromethyl-1,2,4-thiadiazole is described in U.S. Pat. No. 3,917,478, which issued to Moser et al on Nov. 4, 1975, and is prepared by (1) the side-chain fluorination of 5-chloro-3-trichloro methyl a Swart's fluorination mixture consisting of antimony trifluoride, antimony trichloride and chlorine, followed by (2) ammoniation of 5-chloro-3-trifluoromethyl-1,2,4-thiadiazole.

Suitable lower alkyl chlorothiolformate reactants include methyl chlorothiolformate, ethyl chlorothiolformate, n-propyl chlorothiolformate, iso propyl chlorothiolformate, n-butyl chlorothiolformate and isobutyl chlorothiolformate. These reactants may be made from phosgene and desired lower alkyl mercaptan according to conventional known methods.

Any conventional reaction conditions may be employed in the synthesis of the present compounds and the present invention is not intended to be limited to any particular reaction conditions. Advantageously and preferably, the reaction is carried out with about 1 mole to about 2 moles of the chlorothiolformate per mole of the 1,2,4-thiadiazole reactant and in the presence of a suitable organic solvent such as actone or xylene. Acetone is the preferred solvent when an acid acceptor such as potassium carbonate is employed in the reaction mixture. Xylene is preferred when potassium carbonate is not employed. Furthermore, the reaction temperature and time will both depend upon many factors including the exact reactants being employed. In most situations, reaction temperatures from about 0° C. to about 150° C. and reaction times from about 1 hour to 1 week may be preferred. The desired product may be recovered from the reaction mixture by any conventional means, for example, extraction or simply by cooling the reaction mixture and removing the precipitated product by filtration. Finally, it should be noted that while the reaction illustrated by Equation (A) is a preferred method of preparing compounds of the present invention, other synthesis methods may also be employed.

In accordance with the present invention, it has been found that compounds of Formula (I), above, may be used for defoliation or for desiccation of the green parts of plants. They are, in particular, suitable singly, or in mixtures thereof, for the control of weeds. As contemplated herein, the term "weeds" is meant to include not only weeds in the narrow sense, but also in the broad sense, whereby to cover all plants and vegetation considered undesirable for the particular purposes in question. Whether the active compounds according to the present invention act as total or selective herbicides depends essentially on the amount applied, as the artisan will appreciate.

Specifically, in practicing the process of the present invention, undesirable plant and vegetation are contacted with a herbicidally effective amount of the above-mentioned compounds. It is to be understood that the term "herbicidally effect amount" as used in the specification and claims herein is intended to include any amount that will kill or control said undesirable plants and vegetation when either employed by itself (i.e., in full concentration) or in sufficient concentration with a carrier or other substance. Of course, this amount may be constantly changing because of the possible variations in many parameters. Some of these may include: the number and type of plants to be controlled or killed; the type of loci or media to which the present compounds can be applied (e.g., weeds within crop areas, fence lines); degree of effectiveness required; and type of carrier, if any. The step of contacting may be accomplished by applying the present active compounds to the undesirable plants themselves or to the immediate locus or ground surrounding said plants. For most situations, the application of the compounds of the present invention in amounts from about 0.1 pounds per acre to about 10 pounds per acre will be sufficient for selective or total herbicidal effect.

The above-mentioned compounds of the present invention may be formulated and applied by any conventional methods that include using the compounds alone or with a carrier or other substances which may enhance the effectiveness of the chemical or facilitate handling. Moreover, the activity of the present compounds may be broadened by the addition thereto of other known biocides such as fungicides, other herbicides, insecticides and the like.

Specific methods of formulating and applying these active compounds include applying them in the form of dusts, dust or emulsion concentrates, wettable powders, and concentrates, granulates, dispersions, sprays, solutions and the like.

The dusts and dust concentrates are usually prepared by simply grinding together the active compounds of the present invention with a finely divided inert diluent such as walnut flour, diatomaceous earth, fullers earth, attaclay, talc or kaolin. Dusts generally contain from about 1% to about 15% by weight of active compound and dust concentrates usually contain from about 16% to about 75% by weight active compound. In practice, dust concentrates are usually admixed with more inert diluent at the site of use to form dusts before being applied to undesirable plant foliage.

Wettable powders are generally prepared in the same manner as dust concentrates, but usually about 1% to 10% by weight of a dispersing agent, for example, an alkali metal lignosulfonate and about 1% to 10% of a surfactant, such as a non-ionic surfactant, are incorporated in the formulation. For most applications, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application.

It is possible to formulate granulates whereby these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds or more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that such herbicide formulations, the ingredients which may make up such formulations other than the active compounds and the dosages, and means of applying these formulations may include all known and conventional substances, amounts and means, respectively, that are suitable for obtaining the desired herbicidal result. Therefore, such process parameters are not critical to the present invention.

The following examples further illustrate the present invention. All parts and percentages employed therein are by weight unless otherwise indicated.

EXAMPLE 1

5-(Ethyl Thiolcarbamoyl)-3-Trichloromethyl-1,2,4-Thiadiazole

A stirred slurry of 10.9 grams (0.05 mole) 5-amino-3-trichloromethyl-1,2,4-thiadiazole, 7.4 grams (0.06 mole) ethyl chlorothiolformate, and 7.0 grams (0.05 mole) potassium carbonate in 200 milliliters acetone was refluxed at about 56° C. for 5 days. Following filtration of the insolubles, the low boiling materials were distilled in vacuo. The resulting residue was stirred with 0.5 liter water, filtered, and the filtrate acidified to precipitate 4.5 grams (30% yield) pure product; m.p. 132.3° C.

Analysis - Calculated for $C_6H_6Cl_3N_3OS_2$: C, 23.50; H, 1.97; Cl, 34.69; N, 13.71; S, 20.91. Found: C, 23.30; H, 1.97; Cl, 34.44; N, 13.96; S, 20.79.

EXAMPLE 2

5-(Ethyl-N-Methyl Thiolcarbamoyl)-3-Trichloromethyl-1,2,4-Thiadiazole

A solution of 2.9 grams (0.013 mole) 5-methylamino-3-trichloromethyl-1,2,4-thiadiazole and 3.2 grams (0.025 mole) ethyl chlorothiolformate in 75 milliliters xylene was refluxed at about 140° C. for 18 hours. The low boiling materials were distilled in vacuo and the resulting semi-solid triturated with hexane. Filtration of the hexane slurry gave 3.2 grams (80% yield) pure product as residue; m.p. 64.4° C.

Analysis - Calculated for $C_7H_8Cl_3N_3OS_2$: C, 26.22; H, 2.51; Cl, 33.17; N, 13.11; S, 20.00. Found: C, 26.11; H, 2.39; Cl, 33.36; N, 13.31; S, 20.01.

EXAMPLE 3

5-(Ethyl Thiolcarbamoyl)-3-Trifluoromethyl-1,2,4-Thiadiazole

A stirred slurry of 4.2 grams (0.025 mole) 5-amino-3-trifluoromethyl-1,2,4-thiadiazole, 6.2 grams (0.05 mole) ethyl chlorothiolformate, and 6.2 grams (0.045 mole) potassium carbonate in 200 milliliters acetone was refluxed at about 56° C. for 20 hours. Following filtration of the insolubles, the low boiling materials were distilled in vacuo. The resulting residue was stirred with 0.5 liter water, filtered and the filtrate acidified to precipitate 5.2 grams (81% yield) pure product; m.p. 105° C.

Analysis - Calculated for $C_6H_6F_3N_3OS_2$: C, 28.01; H, 2.35; N, 16.34; S, 24.92. Found: C, 28.21; H, 2.31; N, 16.52; S, 24.64.

EXAMPLE 4

Herbicide Screen

The active material made in Example 1 was tested for activity as an effective herbicide by the following method.

A uniform aqueous dispersion of the chemical was made by dissolving the chemical in a solution of acetone containing a non-ionic surfactant in a concentration of 500 ppm. The resulting solution was diluted with water (1:9) to obtain a mixture of 10% acetone, 50 ppm surfactant, 0.208% by weight test candidate made in Example 1, and the balance water; 50 milliliters of this solution applied to a flat of 144 square inches corresponds to 10 lb/acre. If further dilutions were required for testing at lower concentrations, water was added to this stock solution and the surfactant maintained at 50 ppm.

The aqueous solutions containing each chemical were applied to flats seeded with representative monocotyledonous and dicotyledonous plants. The test chemical was applied to one such flat immediately after it was seeded (pre-emergence screening) and to the other flat after the first true plant leaves had developed (post-emergency screening). Response was rated 12 to 21 days after treatment on a scale of 0 to 10, where 0 represents no injury and 10 represents complete kill.

The crops and weeds used for the determination of activity were: Foxtail Millet (Setaria italica), Japanese Millet (Echinochloa crusgalli), Crabgrass (Digitaria sanguinalis), Wild Oats (Avena fatua), Morning Glory (Ipomoea purpurea), Mustard (Brassica nigra), Pigweed (Amaranthus retroflexus), Sesbania (Sesbania exaltata), Velvet Leaf (Abutilon theophrasti), Soybean (Glycine max), Cotton (Gossypium hirsutum), and Tomato (Lycopersicon esculentum).

The herbicidal data for 5-(ethyl thiolcarbamoyl)-3-trichloromethyl-1,2,4-thiadiazole shown on the following table illustrates the activity for the compounds of this invention. The left side of each column shows the pre-emergency rating and the right side, the post-emergence rating.

TABLE I

| General Herbicide Activity At 10 lb/acre | | | | | | | | | | | | | | | | | | | | | | | | |
|---|---|---|---|---|---|---|---|---|---|---|---|---|---|---|---|---|---|---|---|---|---|---|---|---|
| CROPS | | | | | | GRASSES | | | | | | | | BROAD-LEAF WEEDS | | | | | | | | | | |
| Soybean | | Cotton | | Tomato | | Foxtail Millet | | Japanese Millet | | Crabgrass | | Wild Oats | | Morning Glory | | Mustard | | Pigweed | | Sesbania | | Velvet Leaf | |
| 0 | 2 | 0 | 5 | 0 | 10 | 0 | 5 | 0 | 2 | 0 | 7 | 0 | 0 | 0 | 7 | 0 | 5 | 0 | 8 | 0 | 8 | 0 | 5S |

What is claimed is:

1. A compound of the formula

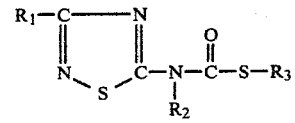

wherein $R_1$ is $CCl_3$ or $CF_3$; $R_2$ is a hydrogen or a lower alkyl group of 1 to 4 carbon atoms; and $R_3$ is a lower alkyl group of 1 to 4 carbon atoms.

2. The compound of claim 1 having the formula

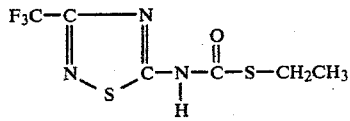

3. The compound of claim 1 having the formula

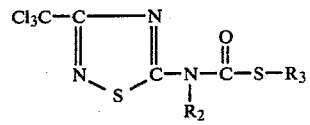

wherein $R_2$ is a hydrogen or a lower alkyl group of 1 to 4 carbon atoms; and $R_3$ is a lower alkyl group of 1 to 4 carbon atoms.

4. The compound of claim 3 having the formula

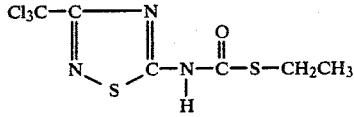

5. The compound of claim 3 having the formula

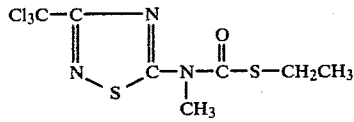

* * * * *